(12) United States Patent
Hoshino et al.

(10) Patent No.: US 7,393,515 B2
(45) Date of Patent: Jul. 1, 2008

(54) FLUORINATED COMPOUND, WATER REPELLENT COMPOSITION AND THIN FILM

(75) Inventors: Taiki Hoshino, Yokohama (JP); Yutaka Furukawa, Yokohama (JP); Takashi Okazoe, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 11/446,200

(22) Filed: Jun. 5, 2006

(65) Prior Publication Data

US 2006/0222865 A1    Oct. 5, 2006

Related U.S. Application Data

(63) Continuation of application No. PCT/JP2004/017966, filed on Dec. 2, 2004.

(30) Foreign Application Priority Data

Dec. 4, 2003    (JP) ............................. 2003-406012

(51) Int. Cl.
  *B01J 3/06*    (2006.01)
  *C07F 7/04*    (2006.01)
(52) U.S. Cl. ........................ 423/446; 556/413
(58) Field of Classification Search ............ None
See application file for complete search history.

(56) References Cited

U.S. PATENT DOCUMENTS 5,274,159 A * 12/1993 Pellerite et al. ............. 556/485
6,821,485 B2   11/2004 Beebe et al.
7,112,397 B2 *  9/2006 Ozaki ..................... 430/270.1

FOREIGN PATENT DOCUMENTS

| JP | 11-344804 | 12/1999 |
| JP | 2000-282240 | 10/2000 |
| JP | 2002-19008 | 1/2002 |
| JP | 2003-321479 | 11/2003 |

OTHER PUBLICATIONS

Anthony V. Lemmo, et al., "Characterization of an Inkjet Chemical Microdispenser for Combinatorial Library Synthesis", Analytical Chemistry, vol. 69, No. 4, Feb. 15, 1997, pp. 543-551.
Younan Xia, et al., "Soft Lithography", Angew. Chem. Int. Ed., 37, Replica molding with a polysiloxane mold provides this patterned microstructure, 1998, pp. 550-575.
Jun Ozaki, et al., Polym. Prepr. Jpn., 49 (12), 2002, pp. 305-306. (with partial English translation).
Nishikawa et al, Science and Technology of Advanced Materials, 2003, vol. 4, No. 1, pp. 81-89.
Zhao et al, J. Am. Chem. Soc., 2002, vol. 124, No. 19 pp. 5284-5285.

* cited by examiner

*Primary Examiner*—Yvonne Eyler
*Assistant Examiner*—M Louisa Lao
(74) *Attorney, Agent, or Firm*—Oblon, Spivak, McClelland, Maier & Neustadt, P.C.

(57) ABSTRACT

To provide a fluorinated compound, which can readily form a thin film having a hydrophobic/hydrophilic pattern, by employing an ultraviolet light having a relatively low energy.

A thin film having a hydrophobic/hydrophilic pattern is formed by irradiating a thin film formed by employing a fluorinated compound represented by the following formula 1 (in the formula 1, each of $R^1$, $R^2$, $R^3$ and $R^4$ which are independent of one another, is a hydrogen atom, a halogen atom or a monovalent organic group, provided that at least one of them is a monovalent organic group having fluorine atoms, and $R^5$ is a hydrogen atom or a monovalent organic group, $R^6$ is a monovalent organic group, and A is a hetero atom) with ultraviolet light Formula 1

$$\begin{array}{c} R^1 \quad R^5 \\ R^2 \diagdown \diagup CH \diagdown A \diagup R^6 \\ R^3 \diagup \diagdown NO_2 \\ R^4 \end{array}$$

17 Claims, 2 Drawing Sheets

FLUORINATED COMPOUND, WATER REPELLENT COMPOSITION AND THIN FILM

TECHNICAL FIELD

The present invention relates to an ultraviolet light-degradable fluorinated compound, a water repellent composition comprising it, a water repellent thin film formed from the composition, and a thin film having a hydrophobic/hydrophilic pattern formed from the thin film.

BACKGROUND ART

At present, as a process for producing fine devices such as semiconductor devices, integrated circuits, devices for organic EL display, it is common to employ a method wherein a thin film of a functional material is formed on a substrate by e.g. vacuum deposition or sputtering, and the thin film is subjected to patterning by photolithography. The photolithography comprises the following steps (1) to (3):

(1) A thin film of a material for patterning is formed on a substrate. (2) A photoresist film is formed on the thin film, and exposure is carried out through a photomask having a predetermined pattern, followed by development with an alkaline developer to form a photoresist pattern. (3) Etching is carried out by using the photoresist pattern as a mask, and an unnecessary part is removed to obtain a thin film having a predetermined pattern configuration. Since the process steps are complex and they have to be carried out in a clean room, the photolithography has had a problem such that the utilization efficiency of energy, material, etc. is low, or the facility tends to be expensive.

A patterning method requiring low cost and energy, has been proposed. For example, ink-jet printing of a solution of a functional material (Non-Patent Document 1) or microcontact printing (Non-Patent Document 2) is being utilized.

Recently, a method has been proposed wherein patterns having different surface characteristics are formed on a substrate, and by utilizing such a difference in the surface characteristics, a fine device is produced. For instance, there is a method wherein a hydrophobic region and a hydrophilic region are formed on a substrate, and an aqueous solution of a functional material is applied on the hydrophilic region. In such a method, the aqueous solution will spread over the hydrophilic region, and it will not exude on the hydrophobic region, whereby a thin film pattern of the functional material can be formed.

As a method for forming regions having different surface characteristics, a method wherein on a substrate having a certain characteristic 1, a thin film having another characteristic 2 is formed, and a part of the thin film is removed to expose the surface having the characteristic 1 thereby to form a surface having the characteristic 1 and characteristic 2, or a method wherein on a region where the thin film having the characteristic 2 is removed, a thin film having a characteristic 3 is formed so as to form a surface having the characteristic 2 and characteristic 3 (Patent Document 1), has been proposed.

The thin film having the characteristic 2 can be removed more efficiently when it is thinner. Accordingly, Self-Assembled Monolayer=SAM (hereinafter referred to as SAM) is preferred. As a patterning method for a thin film such as SAM, a method employing a scanning probe microscope, or a method employing a high energy beam such as ultraviolet light or X-ray, an electron beam, a high-power laser or the like, is known. Among them, a patterning method employing ultraviolet light is preferred in manufacturing, since a substrate having a large area can be treated at once by employing a photomask. However, heretofore, a high energy beam having a wavelength of at most 200 nm has been mainly employed as ultraviolet light, and, for example, in a case where a silicon wafer substrate having a silicon oxide film formed thereon is used, there has been such a problem that even Si—O bond of the substrate is decomposed (Patent Document 2).

As a material which is capable of forming a thin film on a substrate and can be degraded efficiently at a wavelength of at least 300 nm, a 4,5-dimethoxy-2-nitrobenzyl ether compound is known, but the water repellency was not sufficient (Non-Patent Document 3).

Patent Document 1: JP-A-2002-19008
Patent Document 2: JP-A-2000-282240
Non-Patent Document 1: A. V. Lemmo, J. T. Fisher, H. M. Geysen, D, J. Rose, Anal. Chem, 1997, 69, 543-551.
Non-Patent Document 2: Y. Xia, G. M. Whitesides, Angrew. Chem. Int. Ed, 1998, 37, 550-575.
Non-Patent Document 3: Ozaki J, Yamaguchi K, Polymer Material Forum (2002), 305-306.

DISCLOSURE OF THE INVENTION

Object to be Accomplished by the Invention

It is an object of the present invention to solve the above-mentioned problems of prior art, and to provide a fluorinated compound which is capable of being readily degraded by ultraviolet light having a wavelength of at least 300 nm and thus useful for patterning a substrate.

MEANS TO ACCOMPLISH THE OBJECT

The present invention provides a fluorinated compound represented by the following formula 1 (hereinafter referred to as the compound 1):

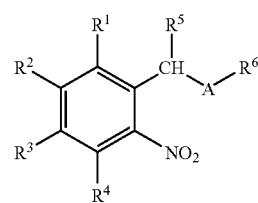

Formula 1

(in the formula 1, each of $R^1$, $R^2$, $R^3$ and $R^4$ which are independent of one another, is a hydrogen atom, a halogen atom, a hydroxyl group, an amino group or a monovalent organic group, provided that at least one of $R^1$, $R^2$, $R^3$ and $R^4$ is a monovalent organic group having fluorine atoms, and $R^5$ is a hydrogen atom or a monovalent organic group, $R^6$ is a monovalent organic group having a hydrolysable group, and A is a hetero atom.)

Further, the present invention provides a water repellent composition comprising the above fluorinated compound and an organic solvent, a water repellent thin film formed by employing the water repellent composition, and a thin film having a hydrophobic/hydrophilic pattern formed by irradiating the water repellent thin film with ultraviolet light and degrading and removing the fluorinated compound at the irradiated portion.

EFFECT OF THE INVENTION

The fluorinated compound of the present invention is readily degraded by irradiation with an ultraviolet light having a relatively low energy. A thin film formed by a composition containing the fluorinated compound is excellent in water repellency. On the other hand, hydrophilicity is imparted to the thin film by degrading the fluorinated compound with ultraviolet light irradiation. By employing such properties, a thin film having a hydrophobic/hydrophilic pattern can be readily formed on a substrate. Accordingly, the thin film having a hydrophobic/hydrophilic pattern can be formed by employing cheaper equipments with fewer process steps.

BEST MODE FOR CARRYING OUT THE INVENTION

Figure 1:
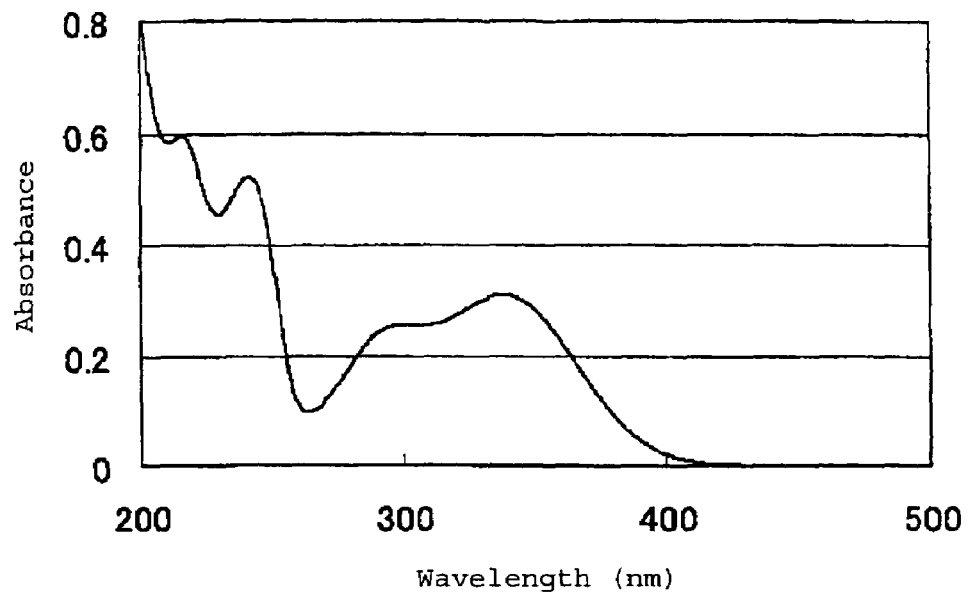
FIG. 1 is an ultraviolet-visible light absorption spectrum of compound e of Preparation Example 1.

In the compound 1 of the present invention, each of $R^1$, $R^2$, $R^3$ and $R^4$, which are independent of one another, is a hydrogen atom, a halogen atom or a monovalent organic group, provided that at least one of them is a monovalent organic group having fluorine atoms. The monovalent organic group having fluorine atoms is preferably a group represented by $R^F$—B—($R^F$ is a polyfluoroalkyl group (hereinafter referred to as $R^F$ group), and B is a bivalent organic group containing no fluorine atom or a covalent bond). $R^F$ group is a group wherein at least 2 hydrogen atoms of an alkyl group are substituted by fluorine atoms. The carbon number of $R^F$ group is preferably 1 to 20, more preferably 4 to 16, most preferably 6 to 12. If the carbon number is within the above range, a thin film to be formed will have an excellent water repellency.

$R^F$ group may be of a linear structure, a branched structure or a cyclic structure, and it is preferably of a linear structure. If $R^F$ group is of a branched structure, the carbon number of the branched moiety is preferably from 1 to 4. Further, $R^F$ group may have an unsaturated bond. $R^F$ group may have halogen atoms other than fluorine atoms, and chlorine atoms are preferred as such other halogen atoms. Further, an etheric oxygen atom or a thioetheric sulfur atom may be inserted in a carbon-carbon bond of $R^F$ group.

The number of fluorine atoms in $R^F$ group, as expressed by (the number of fluorine atoms in $R^F$ group/the number of hydrogen atoms in an alkyl group corresponding to $R^F$ group having the same number of carbon atoms)×100 (%), is preferably at least 60%, particularly preferably at least 80%.

Specific examples of $R^F$ group are shown below, but they are not restricted thereto.

$CF_3$—, $F(CF_2)_2$—, $F(CF_2)_3$—, $F(CF_2)_4$—, $F(CF_2)_5$—, $F(CF_2)_6$—, $F(CF_2)_7$—, $F(CF_2)_8$—, $F(CF_2)_9$—, $F(CF_2)_{10}$—, $F(CF_2)_{11}$—, $F(CF_2)_{12}$—, $F(CF_2)_{13}$—, $F(CF_2)_{14}$—, $F(CF_2)_{15}$—, $F(CF_2)_{16}$—, $(CF_3)_2CF$—, $(CF_3)_2CFCF_2$—, $(CF_3)_2CFCF_2CF_2$—, $(CF_3)_2CFCF_2CF_2CF_2$—, $(CF_3)_2CFCF(CF_3)$—, $(CF_3)_2CFCF(CF_3)CF_2$—, $(CF_3)_2CFCF_2CF(CF_3)$—, $(CF_3)_2CFCF_2CF(CF_3)CF_2CF_2$—, $CF_3CF_2CF(CF_3)$—, $CF_3CF_2CF(CF_3)CF_2CF_2$—, $CF_3CF_2CF(CF_2CF_3)$—, $CF_3CF_2CF(CF_2CF_3)CF_2CF_2$—, $(CF_3)_3C$—, $(CF_3)_3CCF_2$—, $(CF_3)_3C(CF_2CF_3)$—, $(CF_2CF_3)C(CF_3)_2$—, $(CF_2CF_3)_2CCF_3$—.

$CF_2$=CF—, $CF_3CF$=CF—, $CF_3CF_2CF$=CF—, $CF_3CF_2CF_2CF$=CF—, $CF_3CF_2CF_2CF_2CF$=CF—, $CF_3CF_2CF_2CF_2CF_2CF$=CF—, $CF_3CF_2CF_2CF_2CF_2CF_2CF$=CF—, $CF_3C$ $(CF_3)$=CF—, $CF_3C$ $(CF_3)$=C$(CF_3)$—.

$HCF_2$—, $HCF_2CF_2$—, $HCF_2CF_2CF_2$—, $HCF_2CF_2CF_2CF_2$—, $HCF_2CF_2CF_2CF_2CF_2$—, $HCF_2CF_2CF_2CF_2CF_2CF_2CF_2CF_2$—.

$ClCF_2$—, $ClCF_2CF_2$—, $ClCF_2CF_2CF_2$—, $ClCF_2CF_2CF_2CF_2$—, $ClCF_2CF_2CF_2CF_2CF_2$—, $ClCF_2CF_2CF_2CF_2CF_2CF_2$—, $ClCF_2CF_2CF_2CF_2CF_2CF_2CF_2$—, $ClCF_2CF_2CF_2CF_2CF_2CF_2CF_2CF_2$—.

$CF_3OCF_2$—, $CF_3CF_2OCF_2$—, $CF_3OCF_2CF_2$—, $CF_3CF_2OCF_2CF_2$—, $CF_3CF_2OCF_2CF_2OCF_2$—, $CF_3CF_2CCF_2CF_2OCF_2CF_2$—, $CF_3CF_2OCF_2CF_2OCF_2OCF_2$—, $CF_3CF_2OCF_2CF_2OCF_2OCF_2CF_2$—, $CF_3CF_2OCF_2CF_2OCF_2OCF_2CF_2OCF_2$—, $CF_3CF_2OCF_2CF_2OCF_2OCF_2CF_2OCF_2CF_2$—, $CF_3CF_2CF_2OCF_2$—, $CF_3CF_2CF_2CF_2OCF_2$—, $CF_3CF_2CF_2CF_2CF_2OCF_2$—, $CF_3CF_2CF_2OCF_2CF_2$—, $CF_3CF_2CF_2CF_2OCF_2CF_2$—, $CF_3CF_2CF_2CF_2CF_2CF_2OCF_2CF_2$—, $CF_3CF_2CF_2CF_2OCF_2CF_2OCF_2$—, $CF_3CF_2CF_2CF_2CF_2CF_2OCF_2CF_2$—, $CF_3CF_2CF_2CF_2CF_2CF_2OCF_2CF_2OCF_2$—. $CF_3CF_2CF_2CF_2CF_2CF_2OCF_2CF_2OCF_2CF_2$—, $CF_3CF_2CF_2OCF_2CF_2OCF_2CF_2OCF_2$—, $CF_3CF_2CF_2OCF_2CF_2OCF_2CF_2OCF_2CF_2$—, $CF_3CF_2CF_2CF_2OCF_2CF_2OCF_2CF_2OCF_2$—, $CF_3CF_2CF_2CF_2OCF_2CF_2OCF_2CF_2OCF_2CF_2$—, $CF_3CF_2OCF(CF_3)$—, $CF_3CF_2CF_2OCF(CF_3)CF_2$—, $CF_3CF_2CF_2OCF(CF_3)CF_2OCF_2CF_2$—, $CF_3CF_2CF_2OCF(CF_3)CF_2OCF(CF_3)$—, $CF_3CF_2CF_2OCF(CF_3)CF_2OCF(CF_3)CF_2$—.

$CF_3CF_2OCF$=CF—, $CF_3CF_2OCF_2CF_2OCF$=CF—, $CF_3CF_2CF_2OCF$=CF—, $CF_3CF_2CF_2CF_2OCF$=CF—, $CF_3CF_2CF_2CF_2OCF_2CF_2OCF$=CF—, $CF_3CF_2CF_2CF_2CF_2CF_2OCF$=CF—, $CF_3CF_2CF_2CF_2CF_2OCF_2CF_2OCF$=CF—, $CF_3CF_2CF_2OCF(CF_3)CF_2OCF$=CF—.

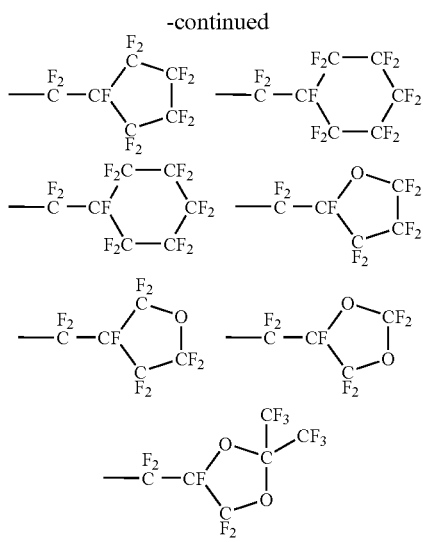

The above-mentioned B is a bivalent organic group or a covalent bond. The bivalent organic group may contain an oxygen atom, a nitrogen atom, a sulfur atom, a phosphorus atom, a chlorine atom, a bromine atom or an iodine atom, may be a saturated group or an unsaturated group, and may be of a linear structure, a branched structure or a cyclic structure. A moiety which bonds to a benzene ring can have a resonance structure, and as a resonance moiety, an oxygen atom, a nitrogen atom, a double bond or a carbonyl group is preferred.

Now, specific examples of $R^F$—B— will be shown below, but they are not restricted thereto.

$R^F$—$(CH_2)_q$O— (q is an integer of from 1 to 10), $R^F$—NH—, $R^F$—$CH_2$NH—, $R^F$—$CH_2CH_2$NH—, $R^F$—$CH_2CH_2CH_2$NH—, $R^F$—$(CH_2)_4$NH—, $R^F$—N$(CH_3)$—, $R^F$—$CH_2$N$(CH_3)$—, $R^F$—$CH_2CH_2$N$(CH_3)$—, $R^F$—$CH_2CH_2CH_2$N$(CH_3)$—, $R^F$—$CH_2CH_2CH_2CH_2$N$(CH_3)$—.

$R^F$—OC(=O)—, $R^F$—$CH_2$OC(=O)—, $R^F$—$CH_2CH_2$OC(=O)—, $R^F$—$CH_2CH_2CH_2$OC(=O)—, $R^F$—$CH_2CH_2CH_2CH_2$OC(=O)—, $R^F$—C(=O)—, $R^F$—$CH_2$C(=O)—, $R^F$—$CH_2CH_2$C(=O)—, $R^F$—$CH_2CH_2CH_2$C(=O)—, $R^F$—$CH_2CH_2CH_2CH_2$C(=O)—, $R^F$—C(=O)O—, $R^F$—$CH_2$C(=O)O—, $R^F$—$CH_2CH_2$C(=O)O—, $R^F$—$CH_2CH_2CH_2$C(=O)O—, $R^F$—$CH_2CH_2CH_2CH_2$C(=O)O—.

$R^F$—C(=O)NH—, $R^F$—$CH_2$C(=O)NH—, $R^F$—$CH_2CH_2$C(=O)NH—, $R^F$—$CH_2CH_2CH_2$C(=O)NH—, $R^F$—$CH_2CH_2CH_2CH_2$C(=O)NH—, $R^F$—CH=CH—, $R^F$—$CH_2$CH=CH—, $R^F$—$CH_2CH_2$CH=CH—.

Among them, $R^F$—$(CH_2)_q$O— (q is an integer of from 1 to 10) is preferred, $R^F$—$(CH_2)_3$O— is more preferred, and $C_8F_{17}(CH_2)_3$O— is most preferred.

In $R^1$, $R^2$, $R^3$ or $R^4$ of the compound 1 of the present invention, a monovalent organic group other than a monovalent organic group having fluorine atoms is preferably a monovalent organic group having an oxygen atom, more preferably an alkoxy group, and may contain a nitrogen atom, a sulfur atom, a phosphorus atom, a chlorine atom, a bromine atom or an iodine atom. The monovalent organic group may be a saturated group or an unsaturated group, and may be of a linear structure, a branched structure or a cyclic structure. The monovalent organic group is preferably a group capable of having a resonance structure with a hetero atom or a benzene ring, since it is excellent in optical absorption properties of benzene ring. The number of monovalent organic groups in $R^1$, $R^2$, $R^3$ or $R^4$ is preferably at least 1.

Specific examples of the monovalent organic groups are not particularly limited, but —$OCH_3$, —$OCH_2CH_3$, —$OCH_2CH_2CH_3$, —$OCH(CH_3)_2$, —$NH(CH_3)$, —$N(CH_3)_2$, —CN, —C(=O)OH, —C(=O)$OCH_3$, —OC(=O)$CH_3$, —NHC(=O)$CH_3$, —N($CH_3$)C(=O)$CH_3$, etc. may preferably be mentioned.

The number of hydrogen atoms in $R^1$, $R^2$, $R^3$ or $R^4$ is preferably at least 1, more preferably at least 2.

In the compound 1 of the present invention, $R^5$ is a hydrogen atom or a monovalent organic group, and a hydrogen atom is preferred. In a case where $R^5$ is a monovalent organic group, it is preferably a lower alkyl group, more preferably a methyl group or an ethyl group. Further, A is a hetero atom, and it is preferably an oxygen atom or a nitrogen atom, more preferably an oxygen atom. In a case where A is an oxygen atom, a thin film after being degraded by ultraviolet light has an excellent hydrophilicity.

In the compound 1, $R^6$ is a monovalent organic group having a hydrolyzable group, may contain an oxygen atom, a nitrogen atom, a sulfur atom, a phosphorus atom, a chlorine atom, a bromine atom or an iodine atom, may be a saturated group or an unsaturated group, and may be of a linear structure, a branched structure or a cyclic structure.

$R^6$ is preferably a group having a silicon atom, more preferably a group represented by —$R^7$—Si$(R^8)_{3-m}X_m$ or —$R^7$—SH ($R^7$ is a bivalent organic group; $R^8$ is a monovalent organic group; X is a hydrolyzable group; and m is an integer of from 1 to 3), most preferably a group represented by —$R^7$—Si$(R^8)_{3-m}X_m$. $R^7$ is preferably a $C_{1-10}$ alkylene group, and —C(=O)— or —NH— may be inserted in a carbon-carbon bond of the alkylene group. $R^8$ is preferably a lower alkyl group. X is preferably an alkoxy group, an acyloxy group, a ketoxime group, an alkenyloxy group, an amino group, an aminoxy group, an amide group, an isocyanate group or a halogen atom, more preferably a halogen atom (specifically a chlorine atom) or an alkoxy group, most preferably an alkoxy group. The alkoxy group is preferably a $C_{1-3}$ alkoxy group, more preferably a methoxy group or an ethoxy group. m is preferably an integer of 2 or 3, more preferably an integer of 3. As the number of m increases, an excellent adhesion will be provided.

As specific examples of the fluorinated compound of the present invention, the following compounds may, for example, be preferably mentioned. Further, in the following compounds, a methyl group and an ethyl group are sometimes referred to as Me and Et, respectively.

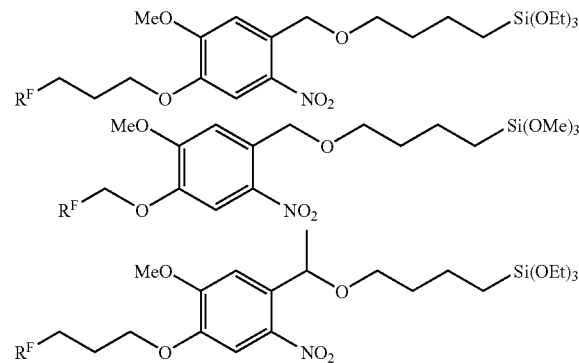

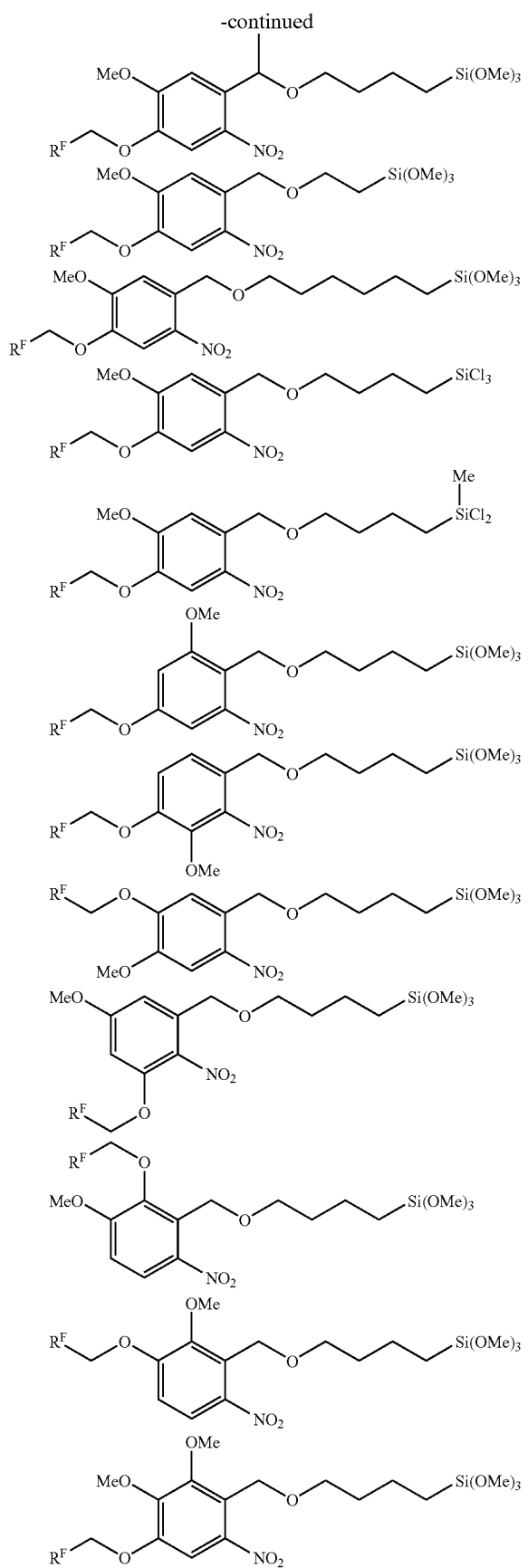
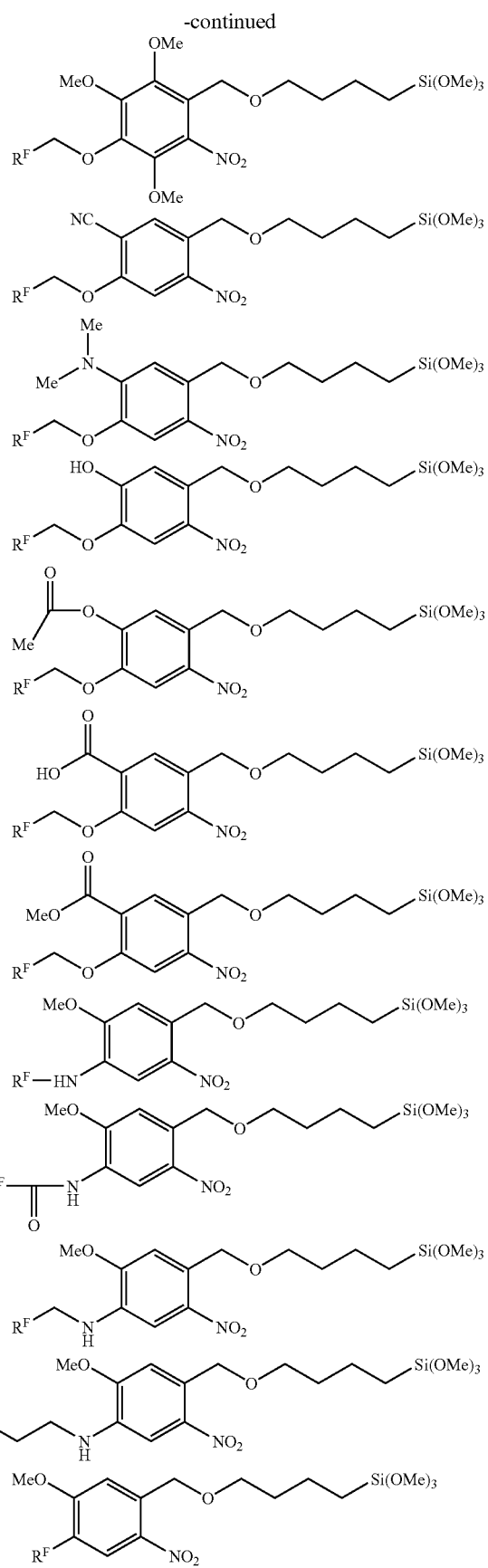

-continued

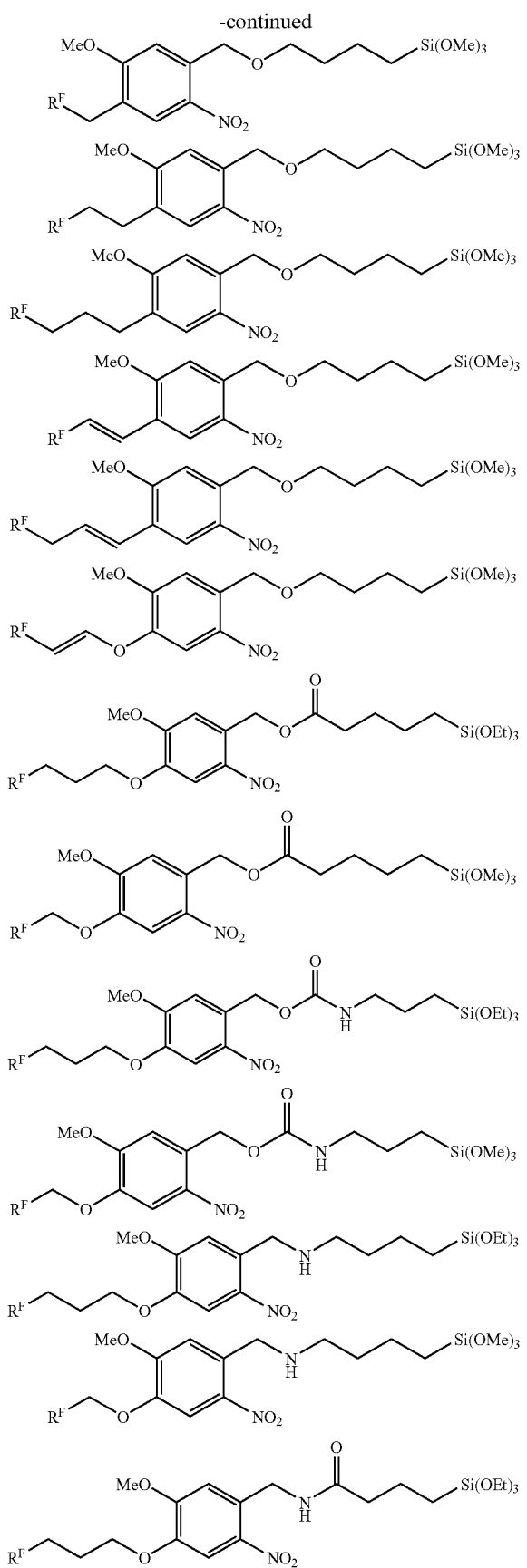

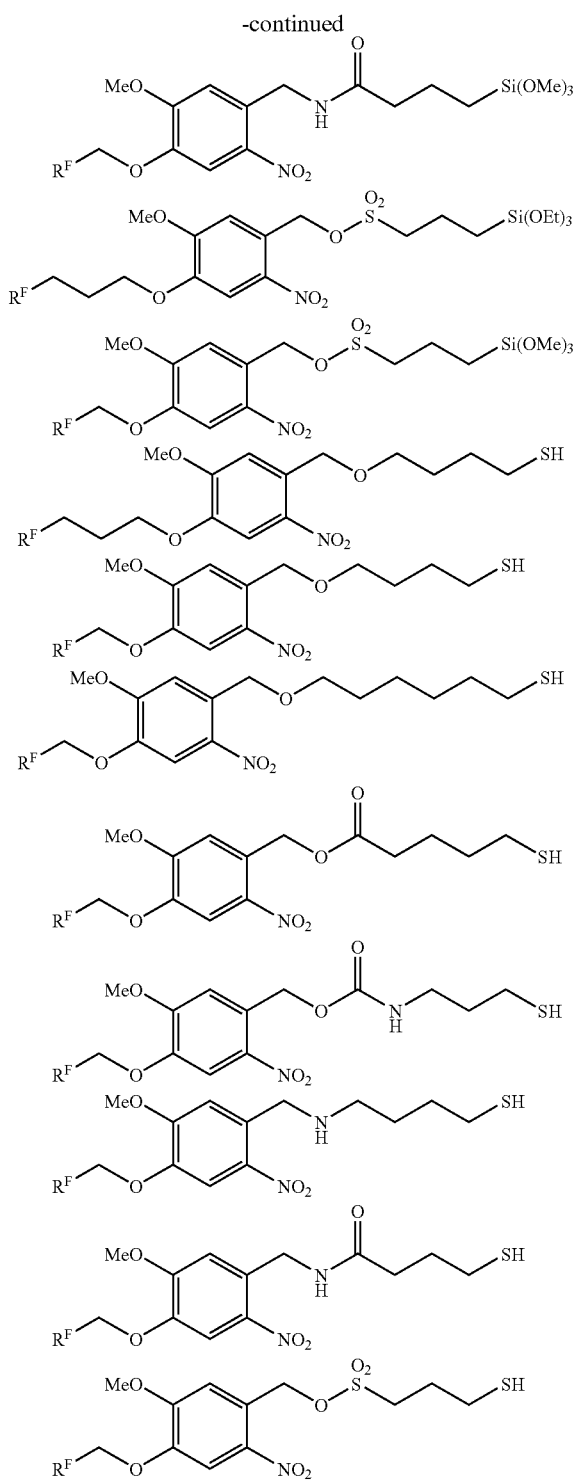

The compound 1 of the present invention contains a monovalent organic group having fluorine atoms, and a thin film formed therefrom has an excellent water repellency. The contact angle to water is preferably at least 100°. The compound 1 is degraded by ultraviolet light, and it is preferred that the thin film after being irradiated by ultraviolet light will have a contact angle to water of at most 80°. This is considered attributable to the fact that by irradiating the compound 1 with ultraviolet light, the compound 1 is degraded into -A-R⁶ and the rest, whereupon -A-R⁶ is converted to a hydroxyl group or an amino group.

The contact angle to water of the thin film formed from the compound 1 is preferably at least 110°. Further, the contact angle to water of the thin film after being degraded by ultraviolet light is preferably at most 70°, most preferably at most 60°. Further, the difference in the contact angle to water of the thin film before and after being degraded by ultraviolet light is preferably at least 30°, more preferably at least 50°.

The water repellent composition of the present invention comprises the compound 1 and an organic solvent. The water repellent composition may contain one or more compounds represented by the formula 1. The organic solvent is not particularly limited, but an alcohol, a ketone, an aromatic hydrocarbon or a paraffinic hydrocarbon is preferred, and a lower alcohol such as ethyl alcohol or 2-propyl alcohol or a paraffinic hydrocarbon is more preferred. The organic solvent may be used alone or in combination as a mixture of two or more of them, whereby the polarity, the evaporation rate, etc. may preferably be adjusted.

The amount of the organic solvent in the water repellent composition is preferably from 0.01 to 1,000 parts by mass, more preferably from 0.1 to 100 parts by mass, per 1 part by mass of the compound 1. If it is within the above range, a uniform thin film will be formed, whereby an excellent water repellency will be provided.

The water repellent composition may contain components other than the compound 1 and the organic solvent. Such other components are preferably acids, and an inorganic acid such as sulfuric acid, hydrochloric acid, nitric acid or phosphoric acid, or an organic acid such as acetic acid, formic acid, p-toluenesulfonic acid or methanesulfonic acid may, for example, be preferably mentioned. By adding the acid, a hydrolyzable group of the compound 1 is converted to a silanol group (Si—OH), then it undergoes a dehydration-condensation reaction on a substrate to form Si—O—Si. At that time, if a Si—OH group is present on the substrate, it reacts thereto as well, whereby adhesion to the substrate will be improved.

The amount of the acid in the water repellent composition is preferably from 0.0001 to 0.1 part by mass, more preferably from 0.001 to 0.01, per 1 part by mass of the compound 1. If it is within the above range, a sufficient hydrolysis efficiency will be provided, and the composition will have an excellent stability. By taking the workability, the thickness of the thin film to be formed, etc. into consideration, the water repellent composition is employed preferably as it is further optionally diluted with an organic solvent.

The water repellent thin film of the present invention is formed by applying the water repellent composition on a substrate. The thickness of the water repellent thin film is not particularly limited, but it is preferably at most 100 nm, more preferably at most 20 nm, most preferably at most 5 nm. The thickness of the hydrophobic/hydrophilic thin film is preferably the thickness of SAM (approximately 1 to 3 nm). If it is within this range, ultraviolet light will be effectively applied to the compound, whereby the degradation reaction will proceed effectively.

As the method for applying the water repellent composition, various known methods such as brush coating, curtain coating, spin coating, dip coating, squeegee coating, spray coating and manual coating may be mentioned. The water repellent composition after being applied on a surface is subjected to drying in the atmosphere, in a nitrogen stream or the like. The drying is preferably carried out at room temperature, and in a case where drying is carried out by heating, the temperature and time for the heating will be set by taking heat resistance of the substrate into consideration.

The thin film having a hydrophobic/hydrophilic pattern of the present invention is formed by irradiating the water repellent thin film with ultraviolet light and degrading and removing the compound 1 at the irradiated portion.

The ultraviolet light to be irradiated has a wavelength of preferably at least 200 nm, more preferably at least 250 nm, most preferably at least 300 nm. If the ultraviolet light has a wavelength of less than 200 nm, it may decompose a material itself that is constituting a substrate. As a light source for the ultraviolet light, a low-pressure mercury lamp, a high-pressure mercury lamp, an ultrahigh-pressure mercury lamp, a xenon lamp, a sodium lamp, a gas laser such as nitrogen, a liquid laser of an organic dye solution or a solid-state laser having a rare earth element ion contained in an inorganic single crystal may, for example, be preferably mentioned. Further, as a light source other than a laser capable of providing a monochromatic light, an ultraviolet light having a desired wavelength, which is obtained by subjecting a broad-band line spectrum or a continuous spectrum to an optical filter such as a band-pass filter and a cut-off filter, may be used. Since a large area can be irradiated at once, a high-pressure mercury lamp or an ultrahigh-pressure mercury lamp is preferred as the light source.

As the irradiating method, a method of irradiating ultraviolet light through a photomask having a predetermined pattern, a method of employing a laser or the like may be mentioned. Since a large area can be irradiated at once, the method of irradiating ultraviolet light through a photomask is preferred.

In the thin film having a hydrophobic/hydrophilic pattern of the present invention, hydrophilicity is exhibited at the portion irradiated with ultraviolet light, and hydrophobicity is exhibited at the portion not irradiated with ultraviolet light. Therefore, in the present invention, by a single application of the water repellent composition to form a thin film, and by a single irradiation of ultraviolet light thereafter, a thin film having a pattern of hydrophilicity and hydrophobicity will readily be obtainable.

The substrate to be employed in the present invention is not particularly limited, but glass, quartz glass, silicon wafer, plastic sheet, metal sheet or the like may preferably be mentioned. Further, a substrate wherein a metal thin film is formed on each of these substrates, may be employed.

EXAMPLES

Now, the present invention will be described in further detail with reference to Examples, but it should be understood that the present invention is by no means restricted thereto. In Examples, AK-225, trade name, manufactured by Asahi Glass Company, Limited, was used as dichloropentafluoropropane (hereinafter referred to as R-225). As a platinum catalyst, a 3 mass % xylene solution of Pt-divinyltetramethyldisiloxane complex was used. Further, NMR spectrum data were shown as apparent chemical shift ranges, and integral values were indicated by ratios. The contact angle to water was obtained as an average value of 3 contact angles measured by putting water droplets on 3 different spots on a substrate by means of sessile drop method.

Preparation Example 1

Preparation Example 1-1

Into a 500 mL reactor made of glass, equipped with a thermometer, a stirrer and a Dimroth condenser, 91 g of $C_8F_{17}CH_2CH_2CH_2Br$ (the purity according to gas chromatography (hereinafter referred to as GC) was 84.3 mol %), 22.7 g of vanillin, 39.0 g of potassium carbonate, 6.87 g of tetrabutylammonium bromide and 170 g of acetonitrile were charged, heated to 82° C. and refluxed for 1.5 hours to conduct the reaction to obtain a reaction crude liquid. Then, to the obtained reaction crude liquid, 450 g of R-225 was added, and the mixture was washed twice with 300 g of distilled water. Then, R-225 as the solvent was distilled off to obtain 109 g of the following compound a. The GC purity was 79.5 mol %, and the yield was 99.5%. The results of $^{19}$F-NMR and $^1$H-NMR are as shown below.

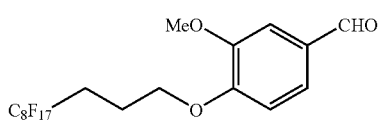

(a)

$^{19}$F-NMR (solvent: $CDCl_3$) δ (ppm): −81.3 (3F), −114.7 (2F), −122.4 (6F), −123.2 (2F), −123.9 (2F), −126.6 (2F).
$^1$H-NMR (solvent: $CDCl_3$) δ (ppm): 2.13-2.42 (4H), 3.90 (3H), 4.16 (2H), 6.93-7.44 (3H), 9.84 (1H).

Preparation Example 1-2

Into a 1L reactor made of glass, equipped with a thermometer, a dropping funnel, a stirrer and a Dimroth condenser, 109 g of the compound a obtained in Preparation Example 1-1 and 330 g of acetic acid were charged, and a solution prepared by mixing 128 g of fuming nitric acid and 105 g of acetic acid was dropwise added thereto over a period of 30 minutes at room temperature. Thereafter, the reaction was further conducted for 3 hours to obtain a reaction crude liquid. Into the obtained reaction crude liquid, 300 g of R-225 was added, and then the mixture was washed with 500 g of distilled water, 500 g of a 8 mass % sodium bicarbonate aqueous solution and 500 g of distilled water. Then, R-225 as the solvent was distilled off to obtain 111.8 g of the following compound b. The GC purity was 73.6 mol %, and the yield was 82.7%. The results of $^{19}$F-NMR and $^1$H-NMR are as shown below.

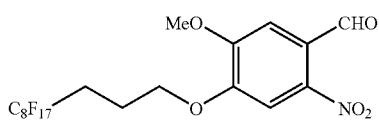

(b)

$^{19}$F-NMR (solvent: $CDCl_3$) δ (ppm): −81.2 (3F), −114.7 (2F), −122.4 (6F), −123.2 (2F), −123.8 (2F), −126.6 (2F).
$^1$H-NMR (solvent: $CDCl_3$) δ (ppm): 2.17-2.43 (4H), 3.99 (3H), 4.21 (2H), 7.40 (1H), 7.58 (1H), 10.44 (1H).

Preparation Example 1-3

Into a 300 mL reactor made of glass, equipped with a thermometer, a stirrer and a Dimroth condenser, 26.8 g of the compound b obtained in Preparation Example 1-2, 3.3 g of hydrazine monohydrate and 150 g of ethanol were charged, heated to 78° C. and refluxed for 3 hours to conduct the reaction. Thereafter, the mixture was cooled to room temperature, and a crude product thereby precipitated was recovered by filtration and washed 5 times with 50 g of ethanol. It was dried under reduced pressure to obtain 17.1 g of the following compound c. The NMR purity was 100 mol %, and the yield was 85.1%. The results of $^1$H-NMR are as shown below.

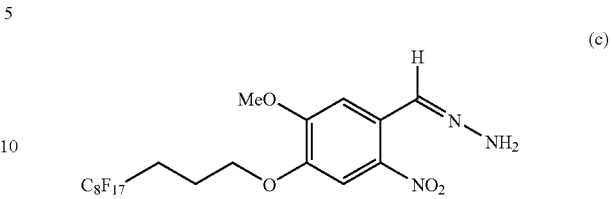

(c)

$^1$H-NMR (solvent: $CDCl_3$) δ (ppm): 2.12-2.39 (4H), 3.95 (3H), 4.13 (2H), 5.81 (2H), 7.48 (1H), 7.55 (1H), 8.41 (1H).

Preparation Example 1-4

Into a 200 mL reactor made of glass, equipped with a thermometer, a stirrer and a Dimroth condenser, 16.8 g of the compound c obtained in Preparation Example 1-3, 10.9 g of manganese oxide (IV) and 100 g of chloroform were charged and reacted for 3 hours with stirring at room temperature to conduct the reaction to obtain a reaction crude liquid. The obtained reaction crude liquid was subjected to filtration, and the filtrate was washed with 100 g of a 8 mass % sodium bicarbonate aqueous solution, followed by drying over 10 g of magnesium sulfate, to obtain a reaction liquid. Into a container made of glass, containing 1.8 g of 3-butene-1-ol, 0.36 g of a 53 mass % tetrafluoroborate aqueous solution and 100 g of chloroform, the total volume of the obtained reaction liquid was dropwise added over a period of 45 minutes under cooling with ice. The reaction was further conducted for 3 hours at room temperature, and chloroform as the solvent was distilled off, then purification by means of column chromatography was carried out to obtain 3.04 g of the following compound d. The yield was 17.0%. The results of $^1$H-NMR are as shown below.

(d)

$^1$H-NMR (solvent: $CDCl_3$) δ (ppm): 2.10-2.44 (6H), 3.62 (2H), 3.93 (3H), 4.13 (2H), 4.88 (2H), 5.04-5.18 (2H), 5.80-5.94 (1H), 7.25 (1H), 7.67 (1H).

Preparation Example 1-5

Into a 50 mL pressure-resistant reactor made of stainless-steel, equipped with an inner bag made of PTFE, 4.60 g of the compound d obtained in Preparation Example 1-4, 2.76 g of triethoxysilane, 29 mg of the Pt catalyst and 15 g of toluene were charged and reacted for 1.5 hours at 100° C. to obtain a reaction crude liquid. Then, toluene as the solvent was distilled off from the obtained reaction crude liquid, and purification was carried out by means of column chromatography to obtain 2.24 g of the following compound e. The NMR purity was 98 mol %, and the yield was 75.3%. The results of $^1$H-NMR are as shown below. The absorption spectrum is shown in FIG. 1.

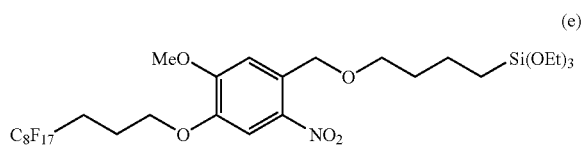

(e)

¹H-NMR (solvent: CDCl₃) δ (ppm): 0.66 (2H), 1.20 (9H), 1.52-1.76 (4H), 2.11-2.42 (4H), 3.59 (2H), 3.78 (6H), 3.95 (3H), 4.14 (2H), 4.86 (2H), 97.30 (1H), 7.69 (1H).

Preparation Example 2

Preparation Example 2-1

Into a 500 mL reactor made of glass, equipped with a thermometer, a stirrer and a Dimroth condenser, 1.13 g of sodium borohydride and 80 g of 2-propanol were charged, and a solution prepared by suspending 26.8 g of the compound b obtained in Preparation Example 1-2 in 200 g of 2-propanol was dropwise added thereto over a period of 20 minutes under cooling with ice. Thereafter, the reaction was conducted for 3 hours with stirring at room temperature to obtain a reaction crude liquid. Into an aqueous solution prepared by dissolving 8.0 g of sodium hydroxide in 300 g of distilled water, the total amount of the obtained reaction crude liquid was poured. Then, 2-propanol as the solvent was removed under reduced pressure, and a product thus obtained was dissolved in 300 g of R-225 and washed 3 times with 200 g of distilled water. Thereafter, R-225 as the solvent was distilled off, and drying was carried out under reduced pressure to obtain a crude product. The obtained crude product was purified by recrystallization to obtain 14.7 g of the following compound f. The NMR purity was 100 mol %, and the yield was 74.5%. The results of ¹H-NMR are as shown below.

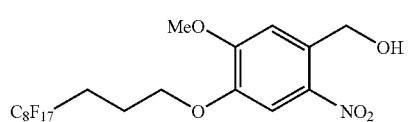

(f)

¹H-NMR (solvent: CDCl₃) δ (ppm): 2.12-2.40 (4H), 2.56 (1H), 3.97 (3H), 4.14 (2H), 4.94 (2H), 7.17 (1H), 7.69 (1H).

Preparation Example 2-2

Into a 100 mL reactor made of glass, equipped with a thermometer, a stirrer and a Dimroth condenser, 6.92 g of the compound f obtained in Preparation Example 2-1, 1.27 g of triethylamine and 50 g of chloroform were charged, and a solution prepared by dissolving 1.37 g of 4-pentenoic acid chloride in 20 g of chloroform was dropwise added thereto over a period of 10 minutes under cooling with ice. Thereafter, the reaction was conducted for 5 hours with stirring at room temperature to obtain a reaction crude liquid. The total amount of the obtained reaction crude liquid was dissolved in 100 g of R-225, then washed with 50 g of distilled water, 50 g of a 8 mass % sodium bicarbonate aqueous solution and 50 g of distilled water in this order. Then, R-225 as the solvent was distilled off, and drying was carried out under reduced pressure to obtain a crude product. The obtained crude product was purified by recrystallization to obtain 4.79 g of the following compound g. The NMR purity was 99.5 mol %, and the yield was 61.5%. The results of ¹H-NMR are as shown below.

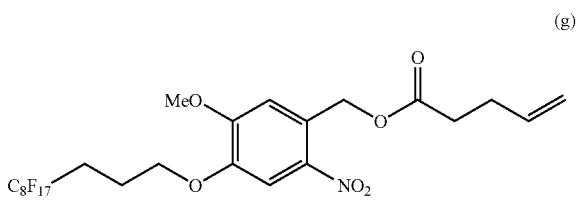

(g)

¹H-NMR (solvent: CDCl₃) δ (ppm): 2.11-2.54 (8H), 3.94 (3H), 4.14 (2H), 4.98-4.90 (2H), 95.50 (2H), 5.70-5.89 (1H), 6.98 (1H), 7.70 (1H).

Preparation Example 2-3

Figure 2:
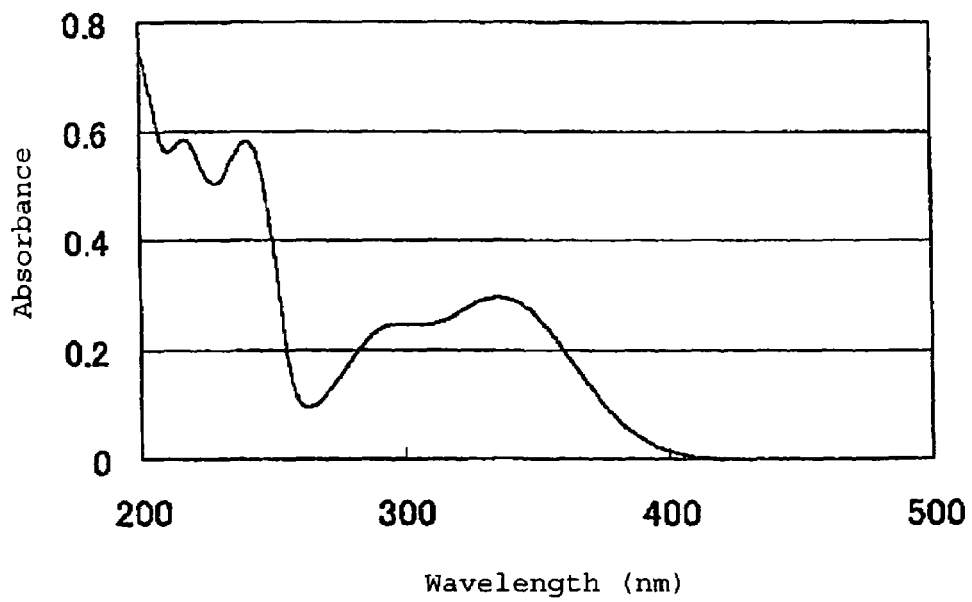
FIG. 2 is an ultraviolet-visible light absorption spectrum of compound h of Preparation Example 2.

Into a 50 mL pressure-resistant reactor made of stainless-steel, equipped with an inner bag made of PTFE, 4.61 g of the compound g obtained in Preparation Example 2-2, 5.18 g of triethoxysilane, 20 mg of the Pt catalyst and 10 g of toluene were charged and reacted for 1 hour at 100° C. to obtain a reaction crude liquid. Then, toluene as the solvent was distilled off from the obtained reaction crude liquid, and purification was carried out by means of column chromatography to obtain 2.86 g of the following compound h. The NMR purity was 99 mol %, and the yield was 50.1%. The results of ¹H-NMR are as shown below. The absorption spectrum is shown in FIG. 2.

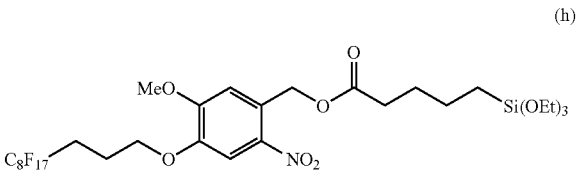

(h)

¹H-NMR (solvent: CDCl₃) δ (ppm): 0.61 (2H), 1.16 (9H), 1.39-1.75 (4H), 2.11-2.43 (6H), 3.79 (6H), 3.95 (3H), 4.15 (2H), 5.48 (2H), 6.98 (1H), 7.69 (1H).

Preparation Example 3

Figure 3:
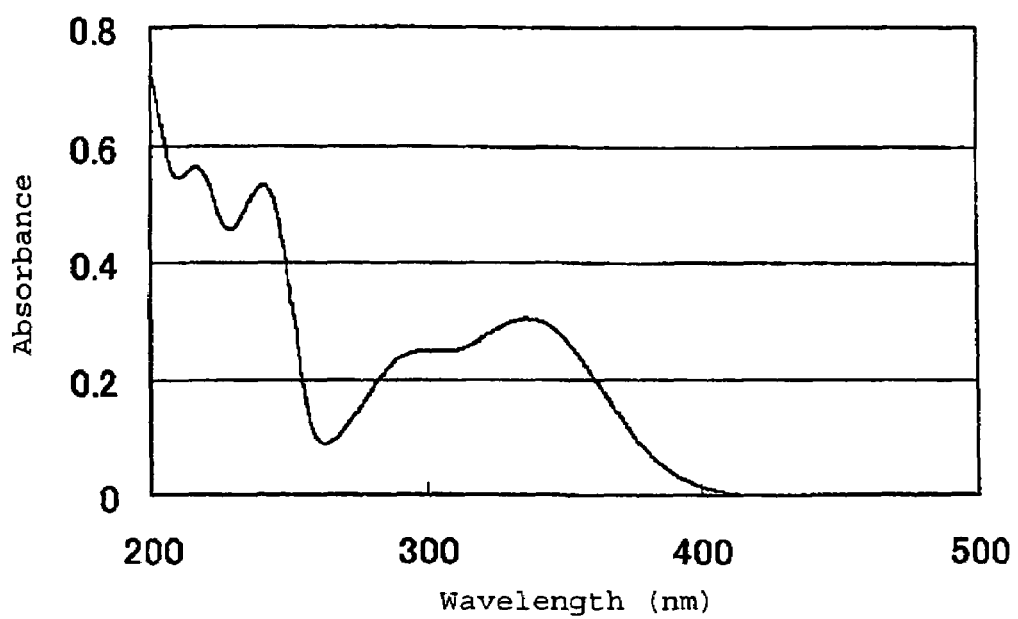
FIG. 3 is an ultraviolet-visible light absorption spectrum of compound i of Preparation Example 3.

Into a 50 mL reactor made of glass, equipped with a thermometer, a stirrer and a Dimroth condenser, 6.00 g of the compound f obtained in Preparation Example 2-1, 2.25 g of 3-isocyanatopropyltriethoxysilane, 46 mg of triethylamine and 25 g of acetonitrile were charged and heated to 80° C. to conduct the reaction for 8 hours to obtain a reaction crude liquid. Then, acetonitrile as the solvent was distilled off from the obtained reaction crude liquid, and drying was carried out under reduced pressure to obtain a crude product. And then, the obtained crude product was purified by means of column chromatography to obtain 3.30 g of the following compound i. The NMR purity was 98 mol %, and the yield was 40.0%. The results of ¹H-NMR are as shown below. The absorption spectrum is shown in FIG. 3.

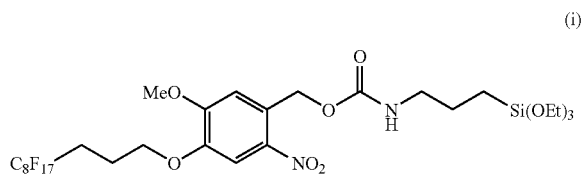

(i)

$^1$H-NMR (solvent: CDCl$_3$) δ (ppm): 0.62 (2H), 1.20 (9H), 1.64 (2H), 2.13-2.39 (4H), 3.20 (2H), 3.80 (6H), 3.93 (3H), 4.13 (2H), 5.12 (2H), 5.48 (2H), 6.99 (1H), 7.68 (1H).

Preparation Example 4

Preparation Example 4-1

Into a 100 mL reactor made of glass, equipped with a thermometer, a stirrer and a Dimroth condenser, 6.02 g of 4,5-dimethoxy-2-nitrobenzyl alcohol, 5.00 g of triethylamine and 30 g of acetone were charged, and a solution prepared by dissolving 5.23 g of 4-pentenoic acid chloride in 10 g of acetone was dropwise added thereto over a period of 15 minutes under cooling with ice. Thereafter, the reaction was conducted for 2 hours with stirring at room temperature to obtain a reaction crude liquid. The total amount of the obtained reaction crude liquid was dissolved in 50 g of R-225 and washed with 30 g of distilled water, 30 g of a 8 mass % sodium bicarbonate aqueous solution and 30 g of distilled water in this order. Then, R-225 as the solvent was distilled off, and drying was carried out under reduced pressure to obtain a crude product. The obtained crude product was purified by recrystallization to obtain 6.76 g of the following compound j. The NMR purity was 99.5 mol %, and the yield was 81.5%. The results of $^1$H-NMR are as shown below.

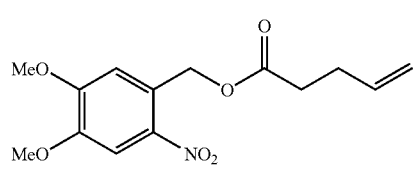

(j)

$^1$H-NMR (solvent: CDCl$_3$) δ (ppm): 2.37-2.54 (4H), 3.94 (6H), 4.98-5.09 (2H), 5.50 (2H), 5.75-5.89 (1H), 6.97 (1H), 7.70 (1H).

Preparation Example 4-2

Into a 50 mL pressure-resistant reactor made of stainless-steel, equipped with an inner bag made of PTFE, 6.46 g of the compound j obtained in Preparation Example 4-1, 10.51 g of triethoxysilane, 60 mg of the Pt catalyst and 15 g of toluene were charged and reacted for 1 hour at 100° C. to obtain a reaction crude liquid. Then, toluene as the solvent was distilled off from the obtained reaction crude liquid, and purification was carried out by means of column chromatography to obtain 6.60 g of the following compound k. The NMR purity was 99 mol %, and the yield was 65.9%. The results of $^1$H-NMR are as shown below.

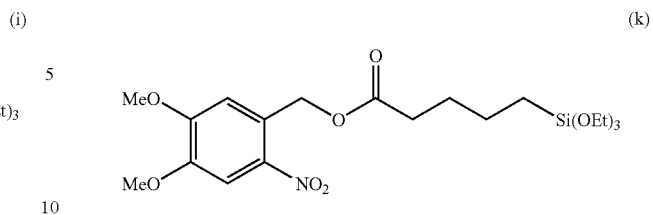

(k)

$^1$H-NMR (solvent: CDCl$_3$) δ (ppm): 0.65 (2H), 1.21 (9H), 1.43-1.78 (4H), 2.43 (2H), 3.81 (6H), 3.97 (6H), 5.51 (2H), 7.00 (1H), 7.72 (1H).

Pretreatment of Glass Substrate

A surface of a 10 cm square soda-lime glass substrate having the thickness of 2 mm was polished and cleaned with a polishing agent containing fine cerium oxide particles. Then, it was rinsed with pure water, followed is by air-drying, to obtain a cleaned glass. In the following Examples, the cleaned glass was employed as a glass substrate.

Pretreatment of Si Wafer Substrate A 5 cm square oxide film-covered Si wafer substrate 20 was dipped in a mixture of a hydrogen peroxide aqueous solution and an ammonium aqueous solution, and subjected to ultrasonic waves for 5 minutes, and then left to stand still for 30 minutes at 60° C. The substrate thus obtained was rinsed with pure water and air-dried to obtain a cleaned Si wafer. In the following Examples, the cleaned Si wafer was employed as a Si wafer substrate.

Example 1

Into a 300 mL container made of glass, 1 part by mass s of the compound e obtained in Preparation Example 1, 100 parts by mass of 2-propanol and 0.5 part by mass of a 0.1 N hydrochloric acid were charged and subjected to hydrolysis for 12 hours at room temperature to obtain a water repellent composition e. 1 mL of the obtained water repellent composition e was dropped on a glass substrate and subjected to spin coating at 3,000 rpm for 20 seconds. Thereafter, it was cleaned with R-225 and air-dried, to prepare a sample e-1.

The obtained sample e-1 had a contact angle to water of 108.8°, and an untreated glass substrate had a contact angle to water of at most 10°. Then, the sample e-1 was irradiated with ultraviolet light by using a high-pressure mercury lamp, cleaned with R-225 and air-dried to prepare a sample e-2. A sample e-21, when the irradiation amount was 22 mJ/cm$^2$, had a contact angle to water of 102.2°. Further, a sample e-22, when an operation of irradiating with the light and cleaning was repeated 12 times so as to have the total irradiation amount of 629 mJ/cm$^2$, had a contact angle to water of 79.8°. Furthermore, a sample e-23, when the irradiation amount was 650 mJ/cm$^2$, had a contact angle to water of 90.9°, and a sample e-24, when an operation of irradiating with the light having the same irradiation amount and cleaning was repeated 5 times so as to have the total irradiation amount of 3,250 mJ/cm$^2$, had a contact angle to water of 62.3°.

As a Comparative Example, the untreated glass substrate was also subjected to an operation of irradiating with ultraviolet light and cleaning, which was repeated 12 times, but it had a contact angle to water of at most 10°.

Example 2

By employing the compound h obtained in Preparation Example 2, a sample h-1 was prepared in the same manner as in Example 1. The obtained sample h-1 had a contact angle to water of 104.9°. A sample h-2 was prepared by irradiation with ultraviolet light in the same manner as in Example 1. A sample h-21, when the irradiation amount was 22 mJ/cm$^2$, had a contact angle to water of 103.1°. Further, a sample h-22, when an operation of irradiating with the light and cleaning was repeated 12 times so as to have the total irradiation amount of 629 mJ/cm$^2$, had a contact angle to water of 76.90°. Further, a sample h-23, when the irradiation amount was 650 mJ/cm$^2$, had a contact angle to water of 86.2°, and a sample h-24, when an operation of irradiating with the light having the same irradiation amount and cleaning was repeated 5 times so as to have the total irradiation amount of 3,250 mJ/cm$^2$, had a contact angle to water of 52.6°.

Example 3

By employing the compound i obtained in Preparation Example 3, a sample i-1 was prepared in the same manner as in Example 1. The obtained sample i-1 had a contact angle to water of 105.8°. A sample I-2 was prepared by irradiation with ultraviolet light in the same manner as in Example 1. A sample i-21, when the irradiation amount was 22 mJ/cm$^2$, had a contact angle to water of 102.6°. Further, a sample i-22, when an operation of irradiating with ultraviolet light and cleaning was repeated 12 times so as to have the total irradiation amount of 629 mJ/cm$^2$, had a contact angle to water of 76.0°. Further, a sample i-23, when the irradiation amount was 650 mJ/cm$^2$, had a contact angle to water of 93.9°, and a sample i-24, when an operation of irradiating with the light having the same irradiation amount and cleaning was repeated 5 times so as to have the total irradiation amount of 3,250 mJ/cm$^2$, had a contact angle to water of 65.8°.

Example 4

A sample u-1 was prepared in the same manner as in Example 1 except that $C_8F_{17}CH_2CH_2Si(OCH_3)_3$ was used instead of the compound e in Example 1. The obtained sample u-1 had a contact angle to water of 105.7°. A sample u-2 was prepared in the same manner as in Example 1 by irradiation with ultraviolet light. A sample u-21, when the irradiation amount was 650 mJ/cm$^2$, had a contact angle to water of 106.6°, and a sample u-22, when an operation of irradiating with the light having the same irradiation amount and cleaning was repeated 5 times so a to have the total irradiation amount of 3,250 mJ/cm$^2$, had a contact angle to water of 105.7°. A compound having no ultraviolet light-degradable group is not degraded.

Example 5

Into a 300 mL container made of glass, 1 part by mass of the compound e obtained in Preparation Example 1, 10 parts by mass of toluene and a Si wafer substrate were charged, followed by refluxing under heating for 1 hour. Thereafter, the Si wafer substrate was recovered, cleaned with R-225 and air-dried to prepare a sample e-3.

The obtained sample e-3 had a contact angle to water of 102.5°, and an untreated Si wafer substrate had a contact angle to water of at most 10°. By employing an ultrahigh-pressure mercury lamp, the sample e-3 was irradiated with ultraviolet light through a filter which blocks a wavelength of at most 300 nm, cleaned with R-225 and air-dried to prepare a sample e-4. A sample e-41, when the irradiation amount was 60 J/cm$^2$, had a contact angle to water of 87.6°. Further, a sample e-42, when an operation of irradiating with the light having the same irradiation amount and cleaning was repeated 15 times so as to have the total irradiation amount of 900 J/cm$^2$, had a contact angle to water of 50.6°.

As a Comparative Example, the untreated Si wafer substrate was also subjected to an operation of irradiating with ultraviolet light and cleaning, which was repeated 15 times, but it had a contact angle to water of at most 10°.

Example 6

By employing the compound h obtained in Preparation Example 2, a sample h-3 was prepared in the same manner as in Example 5.

The obtained sample h-3 had a contact angle to water of 106.4°. A sample h-4 was prepared by irradiation with ultraviolet light in the same manner as in Example 5. A sample h-41, when the irradiation amount was 60 J/cm$^2$, had a contact angle to water of 86.7°. Further, a sample h-42, when an operation of irradiating with the light having the same irradiation amount and cleaning was repeated 15 times so as to have the total irradiation amount of 900 J/cm$^2$, had a contact angle to water of 51.8°.

Example 7

By employing the compound i obtained in Preparation Example 3, a sample i-3 was prepared in the same manner as in Example 5.

The obtained sample i-3 had a contact angle to water of 106.3°. A sample i-4 was prepared by irradiation with ultraviolet light in the same manner as in Example 5. A sample i-41, when the irradiation amount was 60 J/cm$^2$, had a contact angle to water of 82.8°. Further, a sample h-42, when an operation of irradiating with the light having the same irradiation amount and cleaning was repeated 15 times so as to have the total irradiation amount of 900 J/cm$^2$, had a contact angle to water of 53.7°.

Example 8

A sample u-3 was prepared in the same manner as in Example 5 except that $C_8F_{17}CH_2CH_2Si(OMe)_3$ was used instead of the compound e in Example 5.

The obtained sample u-3 had a contact angle to water of 103.4°. A sample u-4 was prepared by irradiation with ultraviolet light in the same manner as in Example 5. A sample u-41, when the irradiation amount was 60 J/cm$^2$, had a contact angle to water of 103.4°. Further, a sample u-42, when an operation of irradiating with the light having the same irradiation amount and cleaning was repeated 15 times so as to have the total irradiation amount of 900 J/cm$^2$, had a contact angle to water of 103.2°. A compound having no ultraviolet light-degradable group is not degraded.

Example 9

The sample h-3 prepared in Example 6 (contact angle: 106.4°) was irradiated with ultraviolet light by using a high-pressure mercury lamp, and it was cleaned with R-225 and air-dried to prepare a sample h-5. A sample h-51, when the irradiation amount was 600 mJ/cm$^2$, had a contact angle to water of 92.4°. Further, a sample h-52, when an operation of irradiating with the light having the same irradiation amount and cleaning was repeated 10 times so as to have the total irradiation amount of 6,000 mJ/cm$^2$, had a contact angle to water of 62.0°.

Example 10

A sample k-1 was prepared in the same manner as in Example 5 except that the compound k obtained in Preparation Example 4 was used instead of the compound e in Example 5.

The obtained sample k-1 had a contact angle to water of 60.2°. A sample k-2 was prepared by irradiation with ultraviolet light in the same manner as in Example 9. A sample k-21, when the irradiation amount was 600 mJ/cm², had a contact angle to water of 53.6°. Further, a sample e-22, when an operation of irradiating with the light is having the same irradiation amount and cleaning was repeated 10 times so as to have the total irradiation amount of 6,000 mJ/cm², had a contact angle to water of 48.8°. In a case where a compound having no fluorine atom is used, no water repellency will be exhibited, and decomposition by irradiation with ultraviolet light will proceed. However, a change in contact angle will be small.

INDUSTRIAL APPLICABILITY

A thin film is formed on a substrate by employing the fluorinated compound of the present invention, and the thin film thus formed is irradiated with ultraviolet light through a photomask having a predetermined pattern, whereby a substrate having a thin film formed thereon, which has a pattern of hydrophobicity and hydrophilicity, will be obtainable. For example, the thin film having the hydrophobic/hydrophilic pattern can readily form a distinct pattern of functional material by injecting a functional material onto a hydrophilic region by means of ink-jet printing. Further, a functional material pattern can be readily formed by forming a functional material film only over the hydrophilic region of a thin film having a hydrophobic/hydrophilic pattern by a method such as vacuum deposition. Such a thin film having the hydrophobic/hydrophilic pattern will be applicable to a stamp for micro-contact printing e.g. by transferring a functional ink, which is contained in the hydrophilic region, to another substrate.

The entire disclosure of Japanese Patent Application No. 2003-406012 filed on Dec. 4, 2003 including specification, claims, drawings and summary is incorporated herein by reference in its entirety.

What is claimed is:

1. A fluorinated compound represented by formula 1:

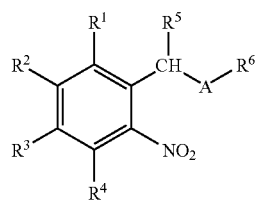

Formula 1 wherein each of $R^1$, $R^2$, $R^3$ and $R^4$ which are independent of one another, is a hydrogen atom, a halogen atom, a hydroxyl group, an amino group or a monovalent organic group, provided that the number of hydrogen atoms is 0, 1 or 2 and that at least one of $R^1$, $R^2$, $R^3$ and $R^4$ is a monovalent organic group having fluorine atoms, $R^5$ is a hydrogen atom or a monovalent organic group, and $R^6$ is a monovalent organic group having a hydrolysable group, and A is a hetero atom.

2. The fluorinated compound according to claim 1, wherein $R^6$ is a group having the formula $—R^7—Si(R^8)_{3-m}X_m$, wherein $R^7$ is a bivalent organic group, $R^8$ is a monovalent hydrocarbon group, X is a hydrolysable group, and m is an integer ranging from 1 to 3.

3. The fluorinated compound according to claim 1, wherein A is an oxygen atom.

4. The fluorinated compound according to claim 1, wherein said monovalent organic group having fluorine atoms has the formula $R^F—B—$, wherein $(R^F)$ is a polyfluoroalkyl group and B is a bivalent organic group that contains no fluorine atoms or is a covalent bond.

5. The fluorinated compound according to claim 4, wherein group $R^F$ has a carbon atom content of 1 to 20 carbon atoms.

6. The fluorinated compound according to claim 4, wherein group $R^F$ has a carbon atom content of 4 to 16 carbon atoms.

7. The fluorinated compound according to claim 4, wherein group $R^F$ contains halogen other than fluorine.

8. The fluorinated compound according to claim 4, wherein the fluorine atoms in group $R^F$ number from at least 80% based on the number of hydrogen atoms in the corresponding alkyl group.

9. The fluorinated compound according to claim 1, wherein each of $R^1$, $R^2$, $R^3$ and $R^4$ which are independent of one another, is a hydrogen atom, a halogen atom, a hydroxyl group, an amino group or a monovalent organic group, and the number of hydrogen atoms is 0, 1 or 2, provided that at least one of $R^1$, $R^2$, $R^3$ and $R^4$ is a monovalent organic group having fluorine atoms and at least one of the remainder of $R^1$, $R^2$, $R^3$ and $R^4$ is a halogen atom, a hydroxyl group, an amino group or a monovalent organic group which bonds to a benzene ring via an oxygen atom, a nitrogen atom, a double bond or a carbonyl group.

10. The fluorinated compound according to claim 1, wherein at least one of $R^1$, $R^2$, $R^3$ and $R^4$ is a monovalent organic group having fluorine atoms and at least one of the remainder of $R^1$, $R^2$, $R^3$ and $R^4$ is a monovalent organic group selected from the group consisting of $—OCH_3$, $—OCH_2CH_3$, $—OCH_2CH_2CH_3$, $—OCH_2(CH_3)_2$, $—NHCH_3$, $—N(CH_3)_2$, $—CN$, $—COOH$, $—C(=O)OCH_3$, $—OC(=O)CH_3$, $—NHC(=O)CH_3$ or $—N(CH_3)C(=O)CH_3$.

11. The fluorinated compound according to claim 1, wherein at least one of $R^1$, $R^2$, $R^3$ and $R^4$ is a monovalent organic group having fluorine atoms and at least one of the remainder of $R^1$, $R^2$, $R^3$ and $R^4$ is an alkoxy group.

12. The fluorinated compound according to claim 1, wherein each of $R^1$, $R^2$, $R^3$ and $R^4$ which are independent of one another, is a hydrogen atom, a halogen atom, a hydroxyl group, an amino group or a monovalent organic group, provided that at least one of $R^1$, $R^2$, $R^3$ and $R^4$ is a group having the formula $R^F—B—$, wherein $R^F$ is a $C_{3—20}$—polyfluoroalkyl group, and B is a bivalent organic group containing no fluorine atoms or is a covalent bond, and at least one of the remainder of $R^1$, $R^2$, $R^3$ and $R^4$ is a monovalent organic group having an oxygen atom, a nitrogen atom, a sulfur atom, a phosphorus atom, a chlorine atom, a bromine atom or an iodine atom.

13. A water repellent composition comprising a fluorinated compound as defined in claim 1, and an organic solvent.

14. The water repellent composition according to claim 13, which has a solvent content of 0.01 to 1,000 parts by mass per part by mass of fluorinated compound.

15. A water repellent thin film formed by applying the water repellent composition as defined in claim 13 on a substrate.

16. The water repellent thin film according to claim 15, which has an applied thickness of at most 100 nm.

17. A thin film having a hydrophobic/hydrophilic pattern formed by irradiating the water repellent thin film as defined in claim 15 with ultraviolet light and degrading and removing the fluorinated compound at the irradiated portion.

* * * * *